(12) United States Patent
Fabre et al.

(10) Patent No.: US 8,207,218 B2
(45) Date of Patent: Jun. 26, 2012

(54) DMAE AS SOLE AGENT FOR THE TREATMENT OF MILD COGNITIVE IMPAIRMENT

(75) Inventors: Pierre Fabre, Castres (FR); Christophe Przybylski, Villefranche de Lauragais (FR); Bruno Dubois, Paris (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 495 days.

(21) Appl. No.: 12/447,816

(22) PCT Filed: Oct. 31, 2007

(86) PCT No.: PCT/EP2007/061737
§ 371 (c)(1),
(2), (4) Date: Apr. 29, 2009

(87) PCT Pub. No.: WO2008/053011
PCT Pub. Date: May 8, 2008

(65) Prior Publication Data
US 2009/0298908 A1 Dec. 3, 2009

(30) Foreign Application Priority Data

Oct. 31, 2006 (FR) ...................................... 06 09548

(51) Int. Cl.
*A61K 31/13* (2006.01)
*A61K 31/4015* (2006.01)
(52) U.S. Cl. ........................................ 514/424; 514/667
(58) Field of Classification Search .................. 514/424, 514/667
See application file for complete search history.

(56) References Cited

U.S. PATENT DOCUMENTS
2006/0211721 A1   9/2006   Roberts

FOREIGN PATENT DOCUMENTS
WO   WO-03/003981 A2   1/2003

OTHER PUBLICATIONS

Souillac et al. Characterization of delivery systems, differential scanning calorimetry, pp. 217-218 (in Encyclopedia of Controlled Drug Delivery, 1999 John Wiley & Sons, pp. 212-227).*
Vippagunta et al. Advanced Drug Delivery Reviews, 48 (2001), pp. 3-26.*
Marsh et al.; "The Effects of Deanol on Cognitive Performance and Electrophysiology in Elderly Humans"; Psychopharmacology; 1979; pp. 99-104; vol. 66, No. 1; Springer Verlag; Berlin, Germany.
Voronina et al.; "Effect of Nicergoline on Learning and Memory"; Methods and Findings in Experimental and Clinical Pharmacology; Jul. 1988; pp. 431-435; vol. 10; No. 7; J.R. Prous; Barcelona, Spain; The Lancet Neurology.
Allain et al.; "Mild Cognitive Impairment: A Treatment at Last?"; Nov. 2004; p. 643; vol. 3; No. 11; Lancet Publishing Group; London, Great Britain.
Dubois et al.; "Amnesic MCI or Prodromal Alzheimer's Disease"; Apr. 2004; pp. 246-248; vol. 3; The Lancet Neurology; Lancet Publishing Group.
Dubois et al.; "Research Criteria for the Diagnosis of Alzheimer's Disease: Revising the NINCDS-ADRDA Criteria"; The Lancet Neurology, Aug. 2007; pp. 734-746; vol. 6; The Lancet.
Van Der Linden et al.; "L'Evaluation des Troubles de la Memoire"; 2004; pp. 24-45; Collection Neuropsychologie; Marseille, France.
Petersen; "Mild Cognitive Impairment as a Diagnostic Entity", Journal of Internal Medicine; 2004; pp. 183-194; vol. 256; Blackwell Publishing Ltd.
Schneider; "Mild Cognitive Impairment"; American Journal of Geriatric Psychiatry; 2005, pp. 629-632; vol. 13; No. 8.
Hughes et al.; "A New Clinical Scale for the Staging of Dementia"; British Journal of Psychiatry: The Journal of Mental Science; Jun. 1982; pp. 566-572; Royal College of Psychiatrists; London, Great Britain.
McKhann et al.; "Clinical Diagnosis of Alzheimer's Disease: Report of the NINCDS-ADRDA Work Group Under the Auspices of Department of Health and Human Services Task Force on Alzheimer's Disease"; Neurology; Jul. 1984; pp. 939-944; vol. 34.
Michel et al..; "Mild Cognitive Impairment"; Neurologies; Mar. 2002; pp. 125-129; vol. 5.
Caffarra et al., "The Effect of Deanol on Amnesic Disorders. A Preliminary Trial". Acta Bio-Med, 1980, pp. 383-389, vol. 51, Ateneo Parmense, Parma, Italy.
Dimpfel et al., "Source Density Analysis of Functional Topographical EEG: Monitoring of Cognitive Drug Action", European Journal of Medical Research, Mar. 19, 1996, pp. 283-290, vol. 1, I. Holzapfel Publishers, Linden, Germany.
Petersen et al., "Mild Cognitive Impairment: Clinical Characterization and Outcome", Arch Neurol., Mar. 1999, pp. 303-308, vol. 56, American Medical Association.
Winblad et al., "Mild Cognitive Impairment—Beyond Controversies, Towards a Consensus: Report of the International Working Group on Mild Cognitive Impairment", Journal of Internal Medicine, 2004, pp. 240-246, vol. 256, Blackwell Publishing Ltd.
Jelic et al., "Clinical Trials in Mild Cognitive impairment: Lessons for the Future", Journal of Neurology, Neurosurgery, and Psychiatry, published online Nov. 23, 2005, jnnp.bmjjournals.
International Search Report, PCT/EP2007/061737, mailed Feb. 6, 2008.
Diagnostic and Statistical Manual of Mental Disorders, 4th Edition, 1994, pp. 684-686.

* cited by examiner

*Primary Examiner* — Jennifer M Kim
(74) *Attorney, Agent, or Firm* — Birch, Stewart, Kolasch & Birch, LLP

(57) ABSTRACT

The present invention relates to the use, as sole active ingredient, of dimethylaminoethanol (DMAE) in free form or in the form of salts or of esters and also of hydrates and solvates thereof, for the manufacture of a medicament for use in the treatment of a non-dementia mild cognitive impairment characterized by an amnestic syndrome of hippocampal type.

9 Claims, 4 Drawing Sheets

DMAE AS SOLE AGENT FOR THE TREATMENT OF MILD COGNITIVE IMPAIRMENT

The present invention concerns the use, as sole active ingredient, of dimethylaminoethanol (deanol or DMAE) in free form, in the form of its salts or esters and their hydrates and solvates, to produce a medicinal product intended for the treatment of non-dementia mild cognitive impairment.

It is therefore important to point out that this use, subject of the present invention, concerns a medicinal product intended for persons and in particular elderly persons with a cognitive complaint (typically a memory complaint) i.e., showing lowered performance levels in cognitive tests (especially memory tests) but whose global cognitive and intellectual functioning is spared and whose activities of daily living remain intact. Such persons are additionally free of any clinical dementia syndromes, and in particular do not meet the clinical criteria for dementia such as defined by DSM-IV (Diagnostic and Statistical Manual of Mental Disorders, $4^{th}$ Edition), by ICD-10 (International Classification of Diseases $10^{th}$ Edition), or for possible or probable Alzheimer's Disease according to NINCDS-ADRDA (National Institute of Neurologic and Communicative Disorders and Stroke (NINCDS) and Alzheimer's Disease and Related Disorders Association (ADRDA) criteria : McKhann G, Drachman D, Folstein M, Katzman R, Price D, Stadlan E M, Clinical Diagnosis of Alzheimer's Disease: report of the NINCDS-ADRDA Work Group under the auspices of the Department of Health and Human Services Task Force on Alzheimer's Disease, Neurology 1984; 34:939-44).

The present invention therefore particularly relates to the use of DMAE in the different above-mentioned forms i.e. in particular in the form of salts or esters chosen from among pyroglutamate, hydrochloride, ascorbate, bitartrate, dihydrogen phosphate, orotate, succinate, carbamate, phenylacetate, benzoate, para-acetamido benzoate and aceglutamate.

According to one particular aspect of the invention, the use of the derivative of DMAE is more particularly intended for the treatment of the hippocampal-type amnesic syndrome.

According to another characteristic of the invention, the derivative of DMAE is more particularly intended for the treatment of moderate cognitive impairment corresponding to stage 0.5 of the scale according to the Clinical Dementia Rating (CDR). This rating was described by Hugues C P, Berg L, Danzinger W L et al in <<A new clinical scale for the staging of dementia>> BrJ Psychiatric 1982; 140; 566-72. This 0.5 stage of the CDR scale corresponds to lowering of the speed of cognitive performance, characterizing a patient having very moderate cognitive impairment but which is nonetheless significant.

The type of the memory disorder in these patients generally translates as slight forgetfulness of no consequence, only partial reconstitution of events with practically undisturbed social behavior, domestic life, leisure activities and intellectual interests.

With practically intact activities of daily living, said patients show absolutely no sign of any dementia.

Since the last half of the last century, several concepts have been put forward in an attempt to isolate indicators for optimal diagnosis with which to better distinguish elderly patients having mild, stable cognitive disorders from those progressing towards dementia, since not all older patients with mild cognitive disorders necessarily develop dementia.

The aim of these concepts is to identify those persons who may benefit from at least preventive, if not palliative or curative management.

These concepts based on different types of approaches (clinical, neuropsychological) and using different diagnosis tools (neuropsychological tests) have in common the presence of a cognitive disorder in the elderly patient.

Having regard to the results obtained and to the proposed mechanism of action, some benefit could also be expected in patients meeting these various assifications. By way of illustration, a list is given below of the main names given in the literature to cognitive disorders in elderly patients:

Prodromal AD
Amnesic MCI (single domain or multiple domain)
Mild Cognitive Impairment (MCI)—Petersen et al (1999)
Cognitively Impaired Non Demented (CIND)—1995
Aging-Associated Cognitive Decline (AACD)—Levy (1994)
Mild Cognitive Decline (MCD)—OMS (1994)
Age-Related Cognitive Decline (ARCD)—DSM IV
Late-Life Forgetfulness (LLF) De Blakford and La Rue
Age-Consistent Memory Impairment (ACMI)
Age-Associated Memory Impairment (AAMI)—Crook et al (1986)
Malignant Senescent Forgetfulness (MSF)
Benign Senescent Forgetfulness (BSF)

One of the most recent names, Mild Cognitive Impairment (MCI) is able to characterize a condition no longer corresponding to normality (age-related cognitive decline considered "normal") but not yet corresponding to dementia (of Alzheimer's disease type). Clinically, MCI applies to a population of elderly patients having a cognitive complaint and theoretically a high risk of progressing towards dementia.

Petersen R C "Mild Cognitive Impairment as a diagnostic entity" J. Intern Med 2004,256:183-194 proposed several definitions of the disorder:

Memory complaint corroborated by close family,
Abnormal impairment considering age,
No dementia,
Cognitive decline,
Essentially normal activities of daily living There is currently a consensus regarding the classification of MCI (syndrome classification) into 4 sub-categories:

amnesic MCI—single-domain (impairment solely regarding memory)
amnesic MCI—multi-domain (impairment in several cognitive areas including memory)
non-amnesic MCI—single-domain (impairment in only one cognitive area other than memory)
non-amnesic MCI—multi-domain (impairment in several cognitive domains but not including memory).

From the viewpoint of progression of the disorder, "single-domain" amnesic MCI and multi-domain amnesic MCI appear to progress chiefly towards dementia of Alzheimer type.

According to one particular characteristic of the invention, the use of the DMAE derivative is more particularly intended for the treatment of mild cognitive impairment such as defined by the International Working Group on Mild Cognitive Impairment in 2004.

It is to be noted that the ethiopathogenic concept has limits however, related firstly to diagnosis conditions which as yet are ill-determined and responsible for data varying greatly from one study to another, and secondly to its etiological heterogeneity.

This makes it difficult to consider a clear therapeutic approach and to predict the development of the disorders in a given individual.

Other definitions have been put forward which tend to individualize and characterize MCI by its mode of progression. "Alzheimer-type MCI" or "Presymptomatic Alzheimer's Disease" is characterized by:
  memory complaint by the person or close family,
  gradual onset: little or no impact on activities of daily living (IADL),
  amnesic syndrome of hippocampal type (poor free recall despite good encoding, impaired delay recall not benefiting from cueing, multiple intrusions),
  persisting memory disorders ascertained on later assessment: no dementia,
  lack of any other potential cause of MCI (if necessary paramedical tests can be carried out: imaging, biology . . . ).

Most of the treatments which have shown some efficacy for Alzheimer's disease have also been tested for MCI, including those products which, in their Marketing Authorization, received an indication for the treatment of Alzheimer's disease (such as anticholinesterases or memantine). It is important to note that, to date, none of these tested products has shown any specific effect in the treatment of MCI.

A list of the chief medications is given below, which have recognized activity in the treatment of Alzheimer disease and whose efficacy has also been tested for MCI:
  Rofecoxib (Merck): 3 then 4 yr, N=1457 conversion to AD, ADAS cog. SRT, CDR, Blessed;
  Donepezil and Vit E (ADCS): 3 yr, N=769 conversion to AD;
  Donepezil (Pfizer): 6 mo, N=269 symptom change;
  Rivastigmine (Novartis): 3, then 4 yr, N=1018 conversion to AD, composite neurocognitive change;
  Piracetam (UCB): 1 yr, N≈600 symptom progression, rate of decline;
  Galantamine (INT-11) (Janssen): 2 yr, N≈900 symptom progression M-ADAS cog, DSST, CDR;
  Galantamine (INT-18) (Janssen): 2 yr, N≈900 symptom progression M-ADAS cog, DSST, CDR and MRI;
  CX 516, AMPA modulator (Cortex, Servier): 1 mo., N=168 Symptomatic.

No experiments conducted with these medications in MCI have shown any significant effect on the main criteria, or on conversion times. Most of these tests were conducted using conversion rate as the main criterion (Schneider, Mild Cognitive Impairment, Am. J. Geriatr. Psychiatry, 2005:13:629-632).

It is thus that the Applicant has unexpectedly ascertained that non-dementia mild cognitive deficiency, in particular MCI, essentially characterized by memory loss only, is a specific model optimally benefiting from the therapeutic effects of DMAE and it salts and other derivatives such as esters, and its hydrates and solvates, showing specific effect on memory improvement.

The target population is individuals presenting with mild cognitive impairment and an amnesic syndrome of hippocampal type, substantiated by deterioration of results for the Grober and Buschke test, also called the 16-item free and cued recall test (FR/CR-16 items) (Van der Linden M et al, L'évaluation des troubles de la mémoire, Eds Solal p 25-45). Therefore this test can be used to select the target population.

The amnesic syndrome of hippocampal type is effectively defined by the following characteristics (Dubois B et al Lancet Neurol., 2004, 246-248; Dubois B et al Lancet Neurol., 2007, 734-746):
  impaired free recall, despite controlled encoding,
  inefficacy of cueing, or impaired recognition indicating a storage defect,
  numerous intrusions.

The Grober and Buschke test can be used to control encoding and retrieval stages to isolate a faulty storage step, which makes it a high performance tool to authenticate an amnesic syndrome of hippocampal type.

This test is conducted as follows:
A list of 16 words (or items) belonging to 16 different semantic categories is to be memorized in 4 phases:
1. A phase in which 16 words are presented 4 by 4, corresponding to a controlled encoding and identification phase of the 16 words with immediate recall, followed by an interference task (20 s, for example counting backwards in ones from 374).
2. A phase with three free recalls and three cued recalls applied to all 16 words (category cueing used for encoding is given for items not freely recalled) with an interference task for 20 seconds between each recall.
3. A recognition phase to recognize the 16 items from among the 16 items, 16 semantic distracters and 16 neutral distracters, and
4. A free/cued recall phase after 20 minutes.

Phase 1: The words are presented four by four on a card i.e. four cards. During the <<encoding>> phase the psychologist presents one card at a time to the patient. For each card of four items the psychologist asks the patient to find an item and read it aloud (e.g. daffodil) which corresponds to the category cue given (e.g. flower). When the four items of a card have been correctly identified, the psychologist withdraws the card and conducts an <<immediate cued recall>> test for the four words: the category cue is said out loud and the patient must remember the item belonging to this category. If some words are not retrieved during this <<immediate cued recall>> the psychologist again shows the corresponding card and gives the name of the category of the non-remembered item so that the patient identifies and reads the target item. Next, the psychologist again conducts an <<immediate cued recall>> hiding the card and asking the patient to remember the item corresponding to the category which had not been found during the first trial. Three <<immediate cued recall>> trials can be proposed for each item. The psychologist proceeds similarly for the three other cards of four items. After presentation and successful immediate cued recall of the fourth card, the patient is asked to carry out an interference task for 20 seconds (counting backwards).

Phase 2: The psychologist then proceeds with the free recall phase during which the patient must remember all the words previously presented on the cards, in any order. This free recall phase lasts two minutes, after which the psychologist moves on to the <<cued recall>> phase solely for those words not remembered during the <<free recall>> phase. The psychologist gives the category for these words to prompt patient recall of the corresponding item. If necessary the psychologist gives the correct reply. The same <<free recall>> and <<cued recall>> procedure, before the interference task, is repeated three times to obtain three recall trials. On the third trial the patient is not corrected.

Phase 3: The psychologist then proposes the <<recognition>> phase immediately after the interference task. The patient must recognize the 16 target items among 32 distracters.

Phase 4: Twenty minutes after the recognition phase, there is a <<free recall>> and <<cued recall>> phase.

The objective of this test is therefore:
  to control attention disorders using the immediate cued recall procedure, to distinguish between the ability to retrieve words spontaneously (free recall) and the ability to store words (cued recall) and consolidate words (cued recall after a period of 20 minutes).

The target population presenting with an amnesic syndrome of hippocampal type is then selected as per the following criteria:
- a free recall score of 20 or less, this score being obtained by counting the items correctly named during the three free recall trials of phase 2, and
- a total recall score of 40 or less, this score being obtained by counting the items correctly named during the three free recall and cued recall trials of phase 2.

Under the present invention, the activity of DMAE and its salts and esters, and the hydrates and solvates, was assessed in a population in whom this memory disorder was induced by injection of scopolamine, to reproduce the profile of the target population.

The Applicant particularly conducted a trial in 24 healthy individuals (cross-over study) on the effects of DMAE and some of its salts and esters, notably DMAE pyroglutamate (pGlu-DMAE), after administering repeated doses for memory loss induced by injection of scopolamine to block cholinergic transmission. The medications given were in forms suitable to be taken via oral route, corresponding to dosage units allowing daily doses in the order of 100 mg to 3 g, advantageously 300 mg to 3 g of active ingredient in adults, particularly in the order of 1500 mg per day. The tested medications led to plasma levels corresponding to a Cmax peak of around 1.5 µg/ml of DMAE and/or around 24 ng/ml of pGlu (pyroglutamic acid).

The Applicant conducted the following tests:
Memory test: Buschke Selective Reminding Test,
Attention test: Digit Symbol Substitution Test (90"),
Assessment of alertness and mood: EVA by Bond and Lader,
Sensory-motor performance tests: reaction times (total, decisional and motor)

The main results observed are given in the graphs of the appended FIGS. 1 to 4 in which:
LTS designates the number of words acquired in long-term storage,
LTR designates the number of words retrieved from long-term memory in each test i.e. the words belonging to LTS and which are recalled for the test in progress, and
CLTR designates the number of words which are consistently acquired i.e. which are recalled during subsequent tests.

Figure 1:
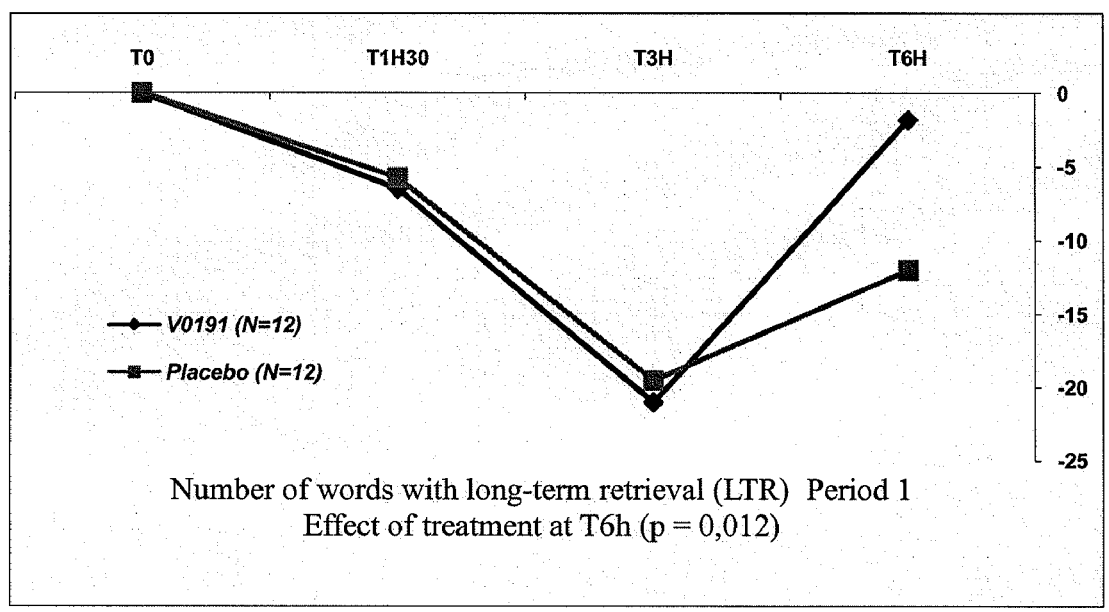
FIG. 1 represents a diagram relative to the number of words retrieved from long-term memory at different times after administration of DMAE or a placebo, each product being tested on 12 persons.
Figure 2:
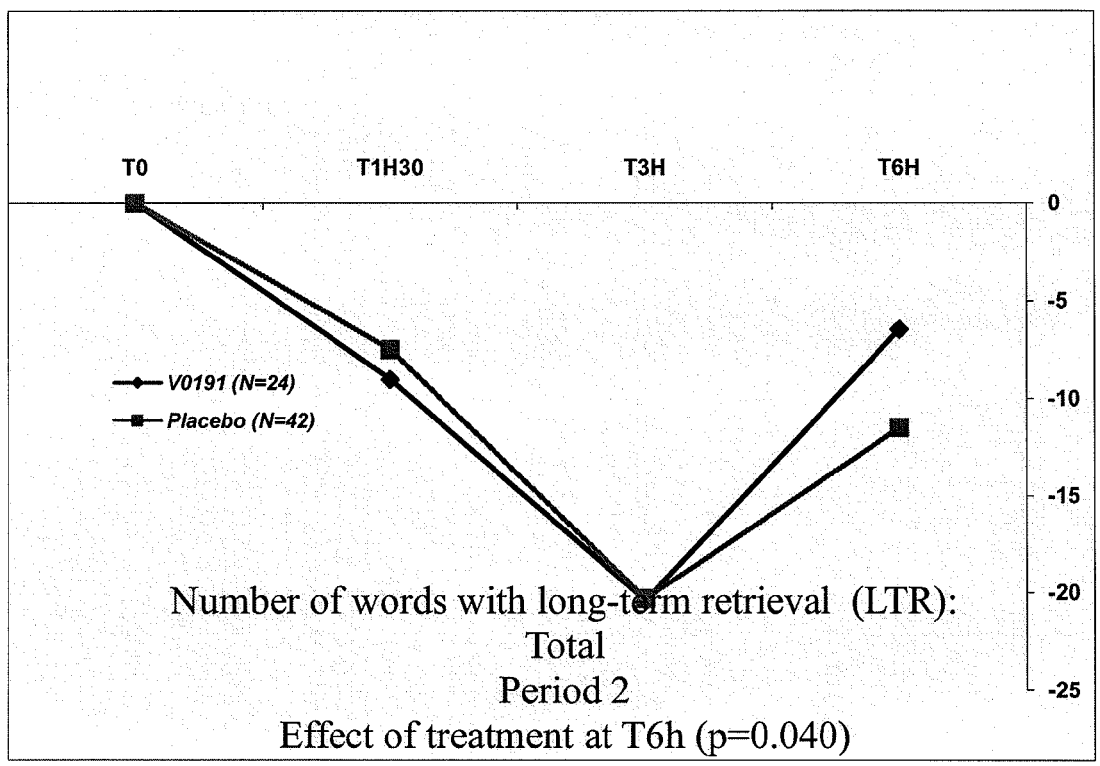
FIG. 2 represents a diagram relative to the number of words retrieved from long-term memory at different times after administration of DMAE or a placebo, the DMAE and the placebo being tested on 24 and 42 persons, respectively.
Figure 3:
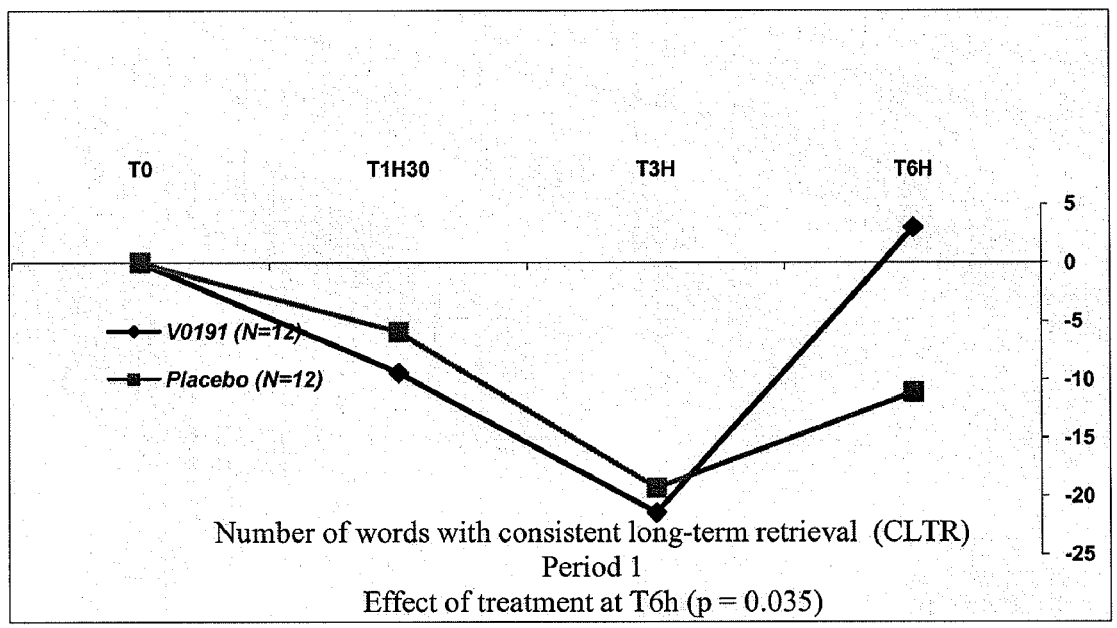
FIG. 3 represents a diagram relative to the number of words which are consistently acquired at different times after administration of DMAE or a placebo, each product being tested on 12 persons.
Figure 4:
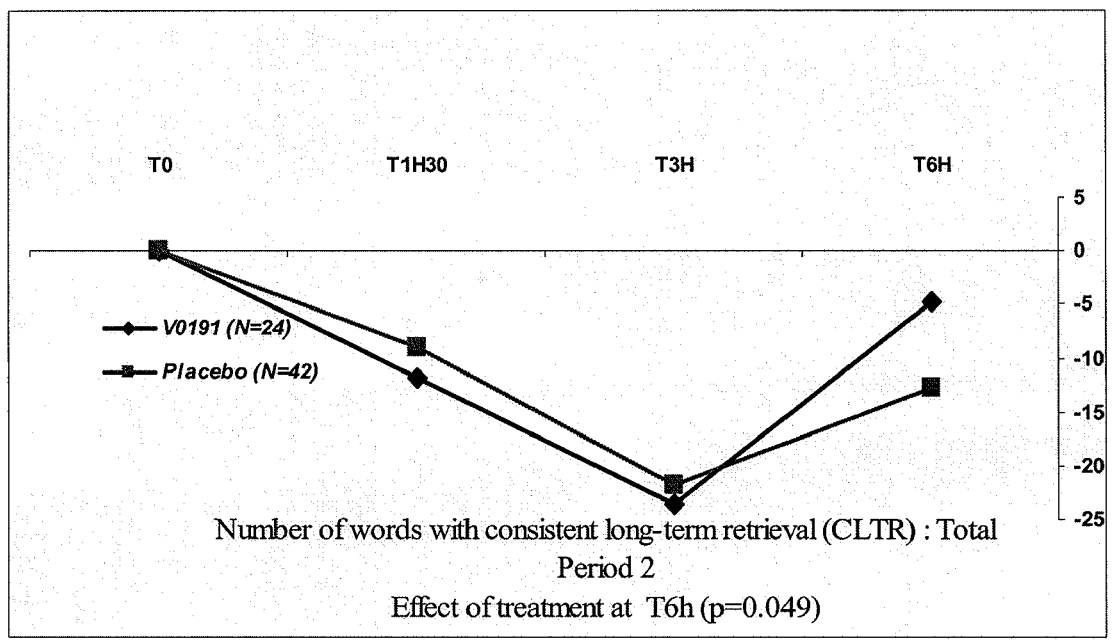
FIG. 4 represents a diagram relative to the number of words which are consistently acquired at different times after administration of DMAE or a placebo, the DMAE and the placebo being tested on 24 and 42 persons, respectively.

DMAE and its derivatives, in particular DMAE pyroglutamate, showed a specific effect on memory performance levels without any impact on the other cognitive components tested such as alertness, attention, etc.

Therefore the mechanism of action of DMAE or its salts appears to be different from that of the above-mentioned conventional anticholinesterases whose effect on memory only appears to be the result of a global effect on various cognitive aspects such as alertness, attention, learning etc.

Subsequent to various other experiments conducted by the Applicant, it appears that DMAE and its salts or esters having procholinergic activity appear to act more specifically via the septo-hippocampal cholinergic route involved in memory processes, rather than on the innominato-cortical cholinergic system more involved in the intention process having regard to its frontal distribution.

The invention claimed is:

1. Method of treatment of non-dementia mild cognitive impairment, characterized by an amnesic syndrome of hippocampal type, which comprises administering an effective amount of a medicinal product comprising dimethylaminoethanol (DMAE) as a sole active ingredient, in free form or in the form of its salts or esters to a person in need thereof.

2. Method according to claim 1, wherein said DMAE is used in the form of a salt or ester chosen from among the following derivatives: pyroglutamate, hydrochloride, ascorbate, bitartrate, dihydrogen phosphate, orotate, succinate, carbamate, phenylacetate, benzoate, para-acetamido benzoate and aceglutamate.

3. Method according to claim 1, wherein said medicinal product is presented in a form intended to be taken via oral route, in a dosage unit allowing a daily dose for adults of 300 mg to 3 g of active ingredient.

4. Method according to claim 3, wherein said medicinal product in is the form of a dosage unit to be taken via oral route, allowing the daily administration of dimethylaminoethanol leading to a plasma level corresponding to a $C_{max}$ of around 1.5 µg/ml of dimethylaminoethanol.

5. Method according to claim 2, wherein said DMAE is deanol pyroglutamate.

6. Method according to claim 5, wherein said medicinal product is presented in a form intended to be taken by oral route in a unit dosage allowing the daily administration to adults of 300 mg to 3 g.

7. Method according to claim 6, wherein said medicinal product is presented in the form of a dosage unit to be taken via oral route, allowing the daily administration of dimethylaminoethanol pyroglutamate leading to a plasma level corresponding to a $C_{max}$ of around 1.5 µg/ml of dimethylaminoethanol and a plasma level corresponding to a $C_{max}$ of around 24 ng/ml of pyroglutamic acid.

8. Method according to claim 3, wherein said daily dose for adults of active ingredient is 1500 mg.

9. Method according to claim 6, wherein said daily dose for adults of deanol pyroglutamate is 1500 mg.

* * * * *